US012806165B2

(12) United States Patent
Tanaka et al.

(10) Patent No.: US 12,806,165 B2
(45) Date of Patent: Nov. 24, 2026

(54) THERAPEUTIC AGENT FOR MALIGNANT MESOTHELIOMA AND METHOD FOR SELECTING PATIENT HAVING MALIGNANT MESOTHELIOMA

(71) Applicant: National University Corporation Tokai National Higher Education and Research System, Nagoya (JP)

(72) Inventors: Ichidai Tanaka, Nagoya (JP); Yuta Kodama, Nagoya (JP)

(73) Assignee: National University Corporation Tokai National Higher Education and Research System, Nagoya (JP)

( * ) Notice: Subject to any disclaimer, the term of this patent is extended or adjusted under 35 U.S.C. 154(b) by 573 days.

(21) Appl. No.: 18/245,712

(22) PCT Filed: Oct. 15, 2021

(86) PCT No.: PCT/JP2021/038161

§ 371 (c)(1),
(2) Date: Mar. 16, 2023

(87) PCT Pub. No.: WO2022/091809

PCT Pub. Date: May 5, 2022

(65) Prior Publication Data

US 2023/0355568 A1 Nov. 9, 2023

(30) Foreign Application Priority Data

Oct. 28, 2020 (JP) ................................ 2020-180412

(51) Int. Cl.
*A61K 31/282* (2006.01)
*A61K 31/5377* (2006.01)
*A61K 31/713* (2006.01)
*A61P 35/00* (2006.01)

(52) U.S. Cl.
CPC ........ *A61K 31/282* (2013.01); *A61K 31/5377* (2013.01); *A61K 31/713* (2013.01); *A61P 35/00* (2018.01)

(58) Field of Classification Search
CPC .............. A61K 31/282; A61K 31/5377; A61K 31/713; A61P 35/00
See application file for complete search history.

(56) References Cited

U.S. PATENT DOCUMENTS

2011/0160159 A1* 6/2011 Ryan ...................... A61K 45/06
514/58
2011/0189237 A1 8/2011 Kumon et al.
2016/0175283 A1 6/2016 Arce
2017/0198292 A1 7/2017 Fan-Minogue
2019/0240293 A1 8/2019 Weinstein et al.

FOREIGN PATENT DOCUMENTS

CN 101128207 A 2/2008
CN 103930132 A 7/2014
JP 2009-013077 A 1/2009
JP 2014-208650 A 11/2014
WO WO 2018/022668 * 2/2018
WO WO 2018/022668 A2 2/2018

OTHER PUBLICATIONS

Bolukbas, S. et al., "Survival after trimodality therapy for malignant pleural mesothelioma: Radical Pleurectomy, chemotherapy with Cisplatin/ Pemetrexed and radiotherapy", Lung Cancer, vol. 71, No. 1, 2011, pp. 75-81 (7 pages).
Kodama, Yuta et al., "Oxytocin receptor is a promising therapeutic target of malignant mesothelioma", Cancer Science, vol. 112, No. 9, 2021, pp. 3520-3532 (13 pages).
Extended European Search Report, dated Mar. 26, 2024 for corresponding European Application No. 21885928.8 (6 pages).
International Search Report, dated Nov. 22, 2021 for corresponding International Application No. PCT/JP2021/038161 with English translation (5 pages).
Written Opinion of the ISA, dated Nov. 22, 2021 for corresponding International Application No. PCT/JP2021/038161 with English translation (4 pages).
Madrazo, Ignacio et al., "Intraventricular Somatostain-14, arginine vasopressin, and oxytocin: analgesic effect in a patient with intractable cancer pain" , Proceedings of the Meeting of the American Society for Stereotactic and Functional Neurosurgery., 1987, vol. 50, pp. 427-431 (5 pages).
China Office action dated Jun. 30, 2025, for corresponding China Application No. 202180063558.2 with English translation (13 pages).
Wayman et al., "Cligosiban, A Novel Brain-Penetrant, Selective Oxytocin Receptor Antagonist, Inhibits Ejaculatory Physiology in Rodents", J Sex Med, 2018;15:1698-1706 (9 pages).
MCE MedChemExpress, Product Data Sheet, "OT-R antagonist 1", Jun. 27, 2019, https://www.doc88.com/p-8435998378161.html (1 page).
Second Chinese Office Action, dated Nov. 13, 2025, for corresponding Chinese Application No. 202180063558.2 (9 pages).

* cited by examiner

*Primary Examiner* — Shirley V Gembeh
(74) *Attorney, Agent, or Firm* — INTELLECTUAL PROPERTY LAW GROUP LLP

(57) ABSTRACT

An object is to provide a therapeutic agent for a malignant mesothelioma and a method for selecting a patient having a malignant mesothelioma having a high expression level of oxytocin receptors. The object can be achieved by a therapeutic agent for a malignant mesothelioma, the therapeutic agent including, as an active ingredient, a compound that targets an oxytocin receptor.

8 Claims, 9 Drawing Sheets

THERAPEUTIC AGENT FOR MALIGNANT MESOTHELIOMA AND METHOD FOR SELECTING PATIENT HAVING MALIGNANT MESOTHELIOMA

CROSS-REFERENCE TO RELATED APPLICATIONS

This application is a U.S. National Phase application, under 35 U.S. C. § 371, of International Application no. PCT/JP2021/038161, with an international filing date of Oct. 15, 2021, and claims priority to Japanese application no. 2020-180412 filed on Oct. 28, 2020, each of which is hereby incorporated by reference for all purposes.

TECHNICAL FIELD

The disclosure of the present application relates to a therapeutic agent for a malignant mesothelioma and a method for selecting a patient having a malignant mesothelioma.

BACKGROUND ART

A malignant mesothelioma is a tumor arising from a mesothelium covering the surface of a pleura, a pericardium, or a peritoneum. More than 80% of malignant mesotheliomas arise in the pleura, and malignant pleural mesotheliomas and malignant peritoneal mesotheliomas result in a poor prognosis.

It is known that most malignant mesotheliomas arising in the pleura or the peritoneum develop due to asbestos exposure and it takes a long time such as 30 years to 40 years for the symptoms to appear. Thus, incidence of malignant mesotheliomas will continue to be on the rise.

The development form of malignant mesotheliomas may be a localized form or a diffuse form. Most malignant mesotheliomas are of the diffuse development form and infiltrate in a disseminated manner along the pleura, the peritoneum, or the like. Although surgery therapy, radiation therapy, chemotherapy, or the like have been employed, no effective treatment method has been established so far, and the prognosis is quite poor. Thus, there has been active development of therapeutic agents or treatment methods for malignant mesotheliomas as disclosed in Patent Literature 1 and Patent Literature 2.

CITATION LIST

Patent Literature

Patent Literature 1: Japanese Patent Application Laid-Open No. 2009-013077

Patent Literature 2: Japanese Patent Application Laid-Open No. 2014-208650

SUMMARY OF INVENTION

Technical Problem

As disclosed in Patent Literature 1 and Patent Literature 2, new therapeutic agents and treatment methods have been reported. However, since therapeutic agents or treatment methods for malignant mesotheliomas have not yet been established, there is a demand for a new therapeutic agent or treatment method. Through an intensive study about development of a new therapeutic agent for malignant mesotheliomas, the disclosure of the present application has newly found that (1) a compound that targets an oxytocin receptor has an effect of suppressing growth of a malignant mesothelioma and that (2) there is a malignant mesothelioma having a high expression level of oxytocin receptors.

That is, an object of the disclosure of the present application is to provide a therapeutic agent for a malignant mesothelioma and a method for selecting a patient having a malignant mesothelioma having a high expression level of oxytocin receptors.

Solution to Problem (1) A therapeutic agent for a malignant mesothelioma, the therapeutic agent including, as an active ingredient, a compound that targets an oxytocin receptor.

(2) The therapeutic agent according to (1) above, wherein the compound is an oxytocin receptor inhibitor.

(3) The therapeutic agent according to (2) above, wherein the oxytocin receptor inhibitor is at least one selected from a group consisting of Cligosiban, OT-R antagonist 1, L368,899 hydrochloride, and Atosiban.

(4) The therapeutic agent according to (2) above, wherein the oxytocin receptor inhibitor is Retosiban.

(5) The therapeutic agent according to (1) above, wherein the compound is a nucleic acid.

(6) The therapeutic agent according to (5) above, wherein the nucleic acid is siRNA or shRNA.

(7) The therapeutic agent according to any one of (1) to (6) above further including an anticancer agent.

(8) The therapeutic agent according to (7) above, wherein the anticancer agent is cisplatin.

(9) The therapeutic agent according to (7) above, wherein the anticancer agent comprises cisplatin and pemetrexed.

(10) A method for selecting a patient having a malignant mesothelioma, the method for selecting comprising:
- a measurement step of measuring an expression level of oxytocin receptors in a malignant mesothelioma tissue;
- a determination step of determining whether or not the expression level of oxytocin receptors is above a threshold; and
- a selection step of selecting a patient having a malignant mesothelioma in which the expression level of oxytocin receptors is above the threshold.

Advantageous Effect

According to the therapeutic agent for a malignant mesothelioma disclosed in the present application, growth of the malignant mesothelioma can be suppressed.

DESCRIPTION OF EMBODIMENTS

Figure 1:
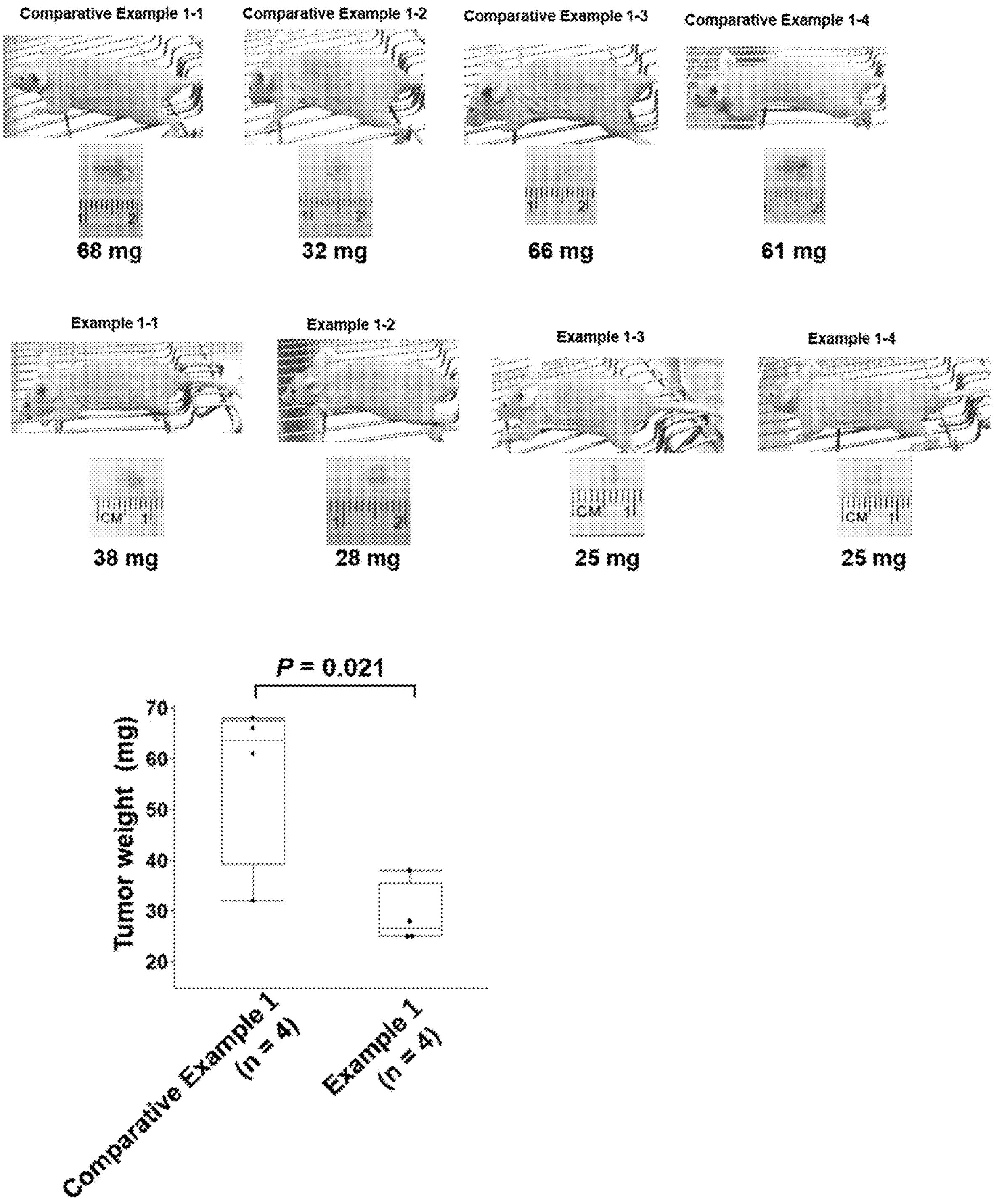
FIG. 1 is a diagram illustrating results of proliferation suppression of malignant mesothelioma cells by Cligosiban using the Xenograft model.

Embodiment of Therapeutic Agent for Malignant Mesothelioma

A therapeutic agent for a malignant mesothelioma (hereafter, which may be simply referred to as "therapeutic agent") according to an embodiment will be described below.

The therapeutic agent according to the embodiment is characterized in containing a compound that targets an oxytocin receptor as an active ingredient.

The above compound is not particularly limited as long as it targets an oxytocin receptor. Note that, in the present specification, "a compound that targets an oxytocin receptor" includes a compound that targets and binds to an oxytocin receptor and a compound that targets and knocks down an oxytocin receptor. The compound that targets an oxytocin receptor may be an oxytocin receptor inhibitor, a nucleic acid such as siRNA, shRNA, or the like that knocks down an oxytocin receptor, an antibody against an oxytocin receptor, or the like.

After an intensive study, the present inventors administered Cligosiban to the Xenograft model of nude mice implanted with malignant mesothelioma cells and thus confirmed an effect of proliferation suppression on malignant mesothelioma cells, as indicated in Examples described later.

Cligosiban is an oxytocin receptor inhibitor used for male premature ejaculation and is a compound expressed by Formula (1) below. Further, it is known that oxytocin receptors on which Cligosiban works are expressed primarily in the mammary gland and the uterus in late pregnancy.

Formula (1)

(1)

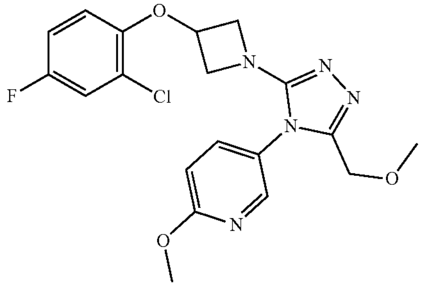

Oxytocin is a peptide hormone secreted from the posterior pituitary gland and composed of nine amino acids and works to contract muscle fibers of the mammary gland to secrete milk, involve contraction of the smooth muscle to contract the uterus during delivery, and the like. Further, although oxytocin was discovered as a hormone specific to the female, it is known that oxytocin is secreted in the male at a certain level.

Because Cligosiban suppressed proliferation of malignant mesothelioma cells, the present inventors have focused on oxytocin receptor inhibitors and conducted in vitro tests for oxytocin receptor inhibitors other than Cligosiban, as illustrated in Examples described later. OT-R antagonist 1 (Formula (2)), L368,899 hydrochloride (Formula (3)), and Atosiban (Formula (4)) expressed by Formula (2) to Formula (4) below are used as the oxytocin receptor inhibitor. As a result, it was confirmed that proliferation of malignant mesothelioma cells was suppressed.

Formulae (2) to (4)

(2)

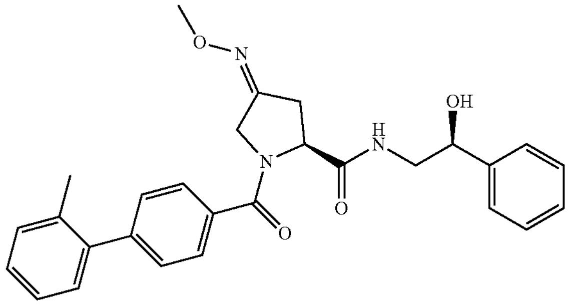

-continued (3)

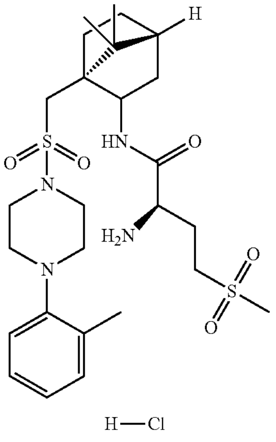

(4)

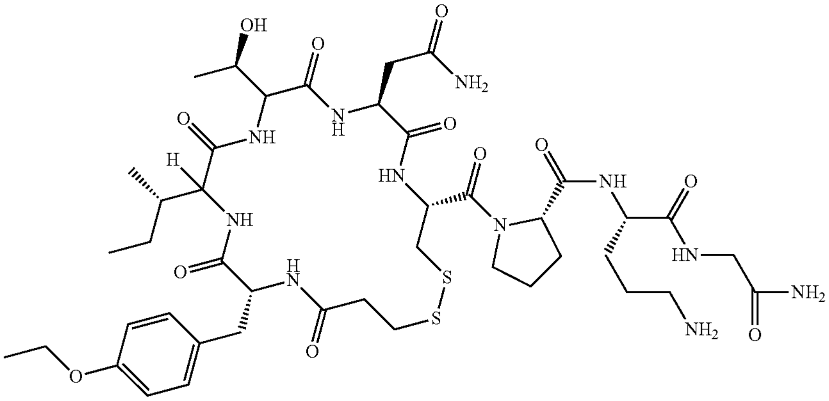

Further, Retosiban expressed by Formula (5) and OT-R antagonist 2 expressed by Formula (6) below are also known as the oxytocin receptor inhibitor. Thus, it is also expected for Retosiban and OT-R antagonist 2 to suppress growth of malignant mesotheliomas.

Formulae (5) and (6)

(5)

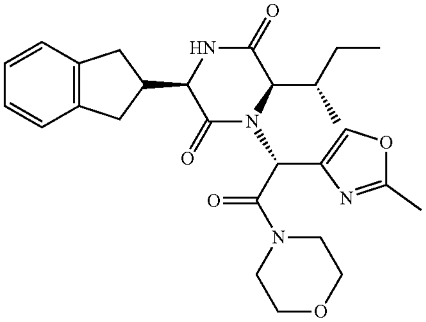

-continued (6)

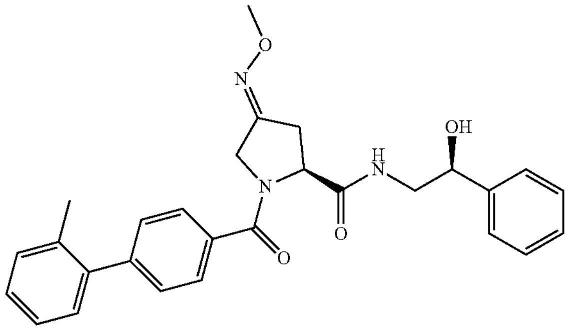

It was confirmed that nucleic acids such as siRNA, shRNA, or the like that knock down oxytocin receptors suppress proliferation of malignant mesothelioma cells, as illustrated in Examples described below. Further, the nucleic acids such as siRNA, shRNA, or the like are not particularly limited as long as they can suppress expression of the oxytocin receptor. It is expected that, with suppression of expression of the oxytocin receptor, growth of malignant mesotheliomas is suppressed.

The antibody against the oxytocin receptor may be a polyclonal antibody or may be a monoclonal antibody. Further, the antibody against the oxytocin receptor may be a complete antibody molecule and may be an antibody fragment that may bind specifically to the oxytocin receptor. The antibody against the oxytocin receptor can be produced by a known method. Further, it is expected that the antibody against the oxytocin receptor suppresses growth of malignant mesotheliomas in the same manner as the oxytocin receptor inhibitor and the siRNA or shRNA that knocks down the oxytocin receptor.

Therefore, the compound that targets an oxytocin receptor can be used for a therapeutic agent for malignant mesotheliomas. Further, one type of the compound that targets an oxytocin receptor may be used alone for the therapeutic agent, or multiple types thereof may be used in combination for the therapeutic agent.

The therapeutic agent according to the embodiment may contain an anticancer agent in addition to the compound that targets an oxytocin receptor. Such use of the compound that targets an oxytocin receptor and an anticancer agent can synergistically enhance the effect of proliferation suppression on malignant mesothelioma cells. The anticancer agent to be added may be a cytotoxic agent (cytotoxic drug), an angiogenesis inhibitor, an immune checkpoint inhibitor, or the like.

The cytotoxic agent is an agent that kills cancer cells, induces cell death, or reduces the proliferation rate/survival rate of cells. The cytotoxic agent may be, for example, an alkylating agent, a platinating agent, an antimetabolite, an antitumor antibiotic, a microtubule polymerization inhibitor, a microtubule depolymerization inhibitor, a topoisomerase inhibitor, a plant alkaloid, a hormonal agent, a bacterial toxin, or the like. The alkylating agent may be, for example, cyclophosphamide, ifosfamide, nitrosourea, dacarbazine, temozolomide, nimustine, busulfan, melphalan, thiotepa, procarbazine, ranimustine, or the like. The platinating agent may be, for example, cisplatin, nedaplatin, oxaliplatin, carboplatin, or the like. The antimetabolite may be, for example, enocitabine, carmofur, capecitabine, tegafur, tegafur-uracil, tegafur-gimeracil-oteracil potassium, gemcitabine, cytarabine, cytarabine okphosphate, nelarabine, fluorouracil, fludarabine, pemetrexed, pentostatin, methotrexate, cladribine, doxyfluridine, hydroxycarbamide, mercaptopurine, or the like. The antitumor antibiotic may be, for example, mytomycin C, doxorubicin, epirubicin, daunorubicin, bleomycin, actinomycin D, aclarubicin, idarubicin, pirarubicin, pepromycin, mitoxantrone, amrubicin, dinostatin stimalamer, or the like. The microtubule polymerization inhibitor may be, for example, vinblastine, vincristine, vinorelbine, vindesine, or the like. The microtubule depolymerization inhibitor may be, for example, paclitaxel, docetaxel, or the like. The topoisomerase inhibitor may be, for example, irinotecan, nogitecan, etoposide, sobuzoxan, or the like. Further, a maytansinoid and a maytansinoid analogs represented by emtansine (DM-1) used for ADC of a molecular-targeting agent that targets cancer are also one of the preferred cytotoxic agents.

The angiogenesis inhibitor is an agent that targets a vascular endothelial proliferation factor and inhibits nutrition supply to cancer cells to suppress proliferation of cancer cells. The angiogenesis inhibitor may be, for example, bevacizumab, ramucirumab, aflibercept, or the like.

The immune checkpoint inhibitor is an agent that binds to inhibitory receptors, which are immune checkpoint molecules, or the ligands thereof, blocks inhibitory signaling, thereby releases brake of the immune system, and enhances the immune response to a tumor. The immune checkpoint inhibitor may be, for example, nivolumab or pembrolizumab that is an anti-PDI antibody, atezolizumab or durvalumab that is an anti-PD-L1 antibody, ipilimumab that is an anti-CTLA4 antibody, or the like.

The compound that targets the oxytocin receptor and the anticancer agent may be used at the same time or may be used with a time difference. It is also possible to separately set administration schedules for both the compound and the anticancer agent and administer respective ones to a target in accordance with the schedule. Furthermore, it is possible to set any number of administration times for both the compound and the anticancer agent and perform a single time or multiple times of the administration. Further, for the anticancer agent used in combination with the compound that targets the oxytocin receptor, a single type thereof may be used, or two or more types thereof may be used in combination.

The method of administering the therapeutic agent according to the embodiment may not be particularly limited as long as it has an advantageous effect on a malignant mesothelioma. The method of administration may be oral, transdermal, intravenous, intramuscular, intrathoracic, intraperitoneal, via a transrectal route, or the like.

The dosage form of the therapeutic agent according to the embodiment may be of, for example, a tablet, a pill, powder, a lozenge, a sachet agent, a cachet agent, an elixir agent, a suspension, an emulsion, a solution, a syrup, an aerosol agent (as a solid or in a liquid medium), an ointment, gelatin soft and hard capsules, a suppository, a sterile injectable solution, sterile sealed powder, or the like.

Further, the therapeutic agent according to the embodiment may contain a conventionally used additive, where necessary. The additive may be an existing additive such as, for example, an excipient, a binder, a lubricant, a disintegrant, an odorant, a solvent, a stabilizer, a base, a wetting agent, or a preservative but is not limited thereto.

The therapeutic agent according to the embodiment achieves the following advantageous effects.

(1) The therapeutic agent containing a compound that targets an oxytocin receptor as an active ingredient suppresses proliferation of malignant mesothelioma cells.

(2) The therapeutic agent further contains an anticancer agent and thereby synergistically suppresses proliferation of malignant mesothelioma cells.

Embodiment of Method for Selecting Patient Having Malignant Mesothelioma

A method for selecting a patient having a malignant mesothelioma according to the embodiment will be described below.

The method for selecting a patient having a malignant mesothelioma according to the embodiment includes (1) a measurement step of measuring the expression level of oxytocin receptors in a malignant mesothelioma tissue, (2) a determination step of determining whether or not the expression level of oxytocin receptors is above a threshold, and (3) a selection step of selecting a patient having a malignant mesothelioma in which the expression level of oxytocin receptors is above the threshold. Further, this method for selection is performed in the order of (1), (2), and (3).

The method of the measurement of the expression level of oxytocin receptors in a malignant mesothelioma tissue in the measurement step is not particularly limited as long as it is possible to measure the expression level of oxytocin receptors. The method of measuring the expression level of oxytocin receptors may be, for example, a polymerase chain reaction (PCR), reverse transcription-PCR (RT-PCR), a northern blot, a microarray, a DNA chip, an RNA chip, or the like.

The determination step determines whether or not the expression level of oxytocin receptors measured in the measurement step is above a threshold. The threshold in the determination step may be set as appropriate.

The selection step selects a patient having a malignant mesothelioma tissue in which the expression level of oxytocin receptors is determined to be above the threshold in the determination step.

The method for selecting a patient having a malignant mesothelioma according to the embodiment achieves the following advantageous effect.

(1) It is possible to select a patient having a malignant mesothelioma having a high expression level of oxytocin receptors in a malignant mesothelioma tissue. It is therefore possible to perform companion diagnosis on a therapeutic agent containing a compound that targets oxytocin receptors as an active ingredient.

Although Examples are presented below to specifically describe the embodiment disclosed in the present application, these Examples are for mere illustration of the embodiment, which are intended neither to limit the scope of the invention disclosed in the present application nor to express limitation of the same.

EXAMPLE

Proliferation Suppression of Malignant Mesothelioma Cell with Cligosiban Using Xenograft Model

Example 1

It was examined whether or not Cligosiban suppresses proliferation of malignant mesothelioma cells in vivo.

The procedure is illustrated below.

(1) $5.0\times10^6$ cells of malignant mesothelioma cell line NCI-H2052 (purchased from ATCC) were administered to the subcutaneous left buttock of nude mice (BALB/c nude (nu/nu) female, 6 to 8 weeks old: purchased from Charles River Japan).

(2) After 3 days from the subcutaneous administration, oral administration of Cligosiban (purchased from MedChemExpress) was started, and the oral administration was applied at each dose of 60 mg/kg every other day for a total of 10 doses.

(3) After one week from the tenth oral administration, the nude mice were dissected, and the subcutaneous tumor weights were measured.

Comparative Example 1

The same procedure as that in Example 1 was applied except that no Cligosiban was administered.

FIG. 1 illustrates the results. Note that four nude mice were used in Example 1. Thus, respective nude mice are denoted as Example 1-1 to Example 1-4. Further, the same applies to Comparative example 1. As can be seen from FIG. 1, it was demonstrated that the subcutaneous tumor weight of Example 1 with administration of Cligosiban is smaller than that of Comparative example 1 without administration of Cligosiban. Further, it was demonstrated that Example 1 suppresses growth of the subcutaneous tumor statistically, significantly compared to Comparative example 1. It was therefore demonstrated that Cligosiban that targets oxytocin receptors can be used as a therapeutic agent for malignant mesotheliomas.

Expression Analysis of Oxytocin Receptor in Patient Having Malignant Mesothelioma

Example 2

From the result of Example 1, proliferation of malignant mesothelioma cells was suppressed by Cligosiban that is an oxytocin receptor inhibitor. Accordingly, expression of oxytocin receptors in a malignant mesothelioma was analyzed.

A database was used to analyze 87 cases of patients having malignant mesotheliomas. As the database, a database "The Cancer Genome Atlas (TCCA; https://www.cancer.gov/about-nci/organization/ccg/research/structural-genomics/tcga)" was used which was resulted from exhaustive analysis about genome methylation abnormalities and gene/protein expression abnormalities.

Figure 2A:
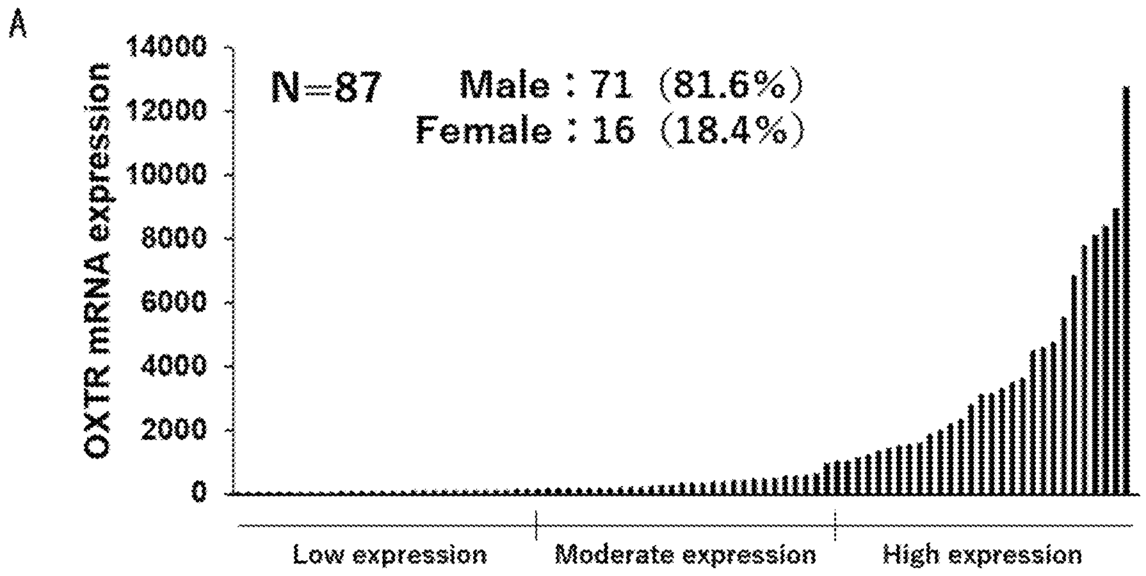
FIG. 2A is a diagram illustrating the expression level of oxytocin receptors in malignant mesothelioma tissues for 87 cases of patients having malignant mesotheliomas.
Figure 2B:
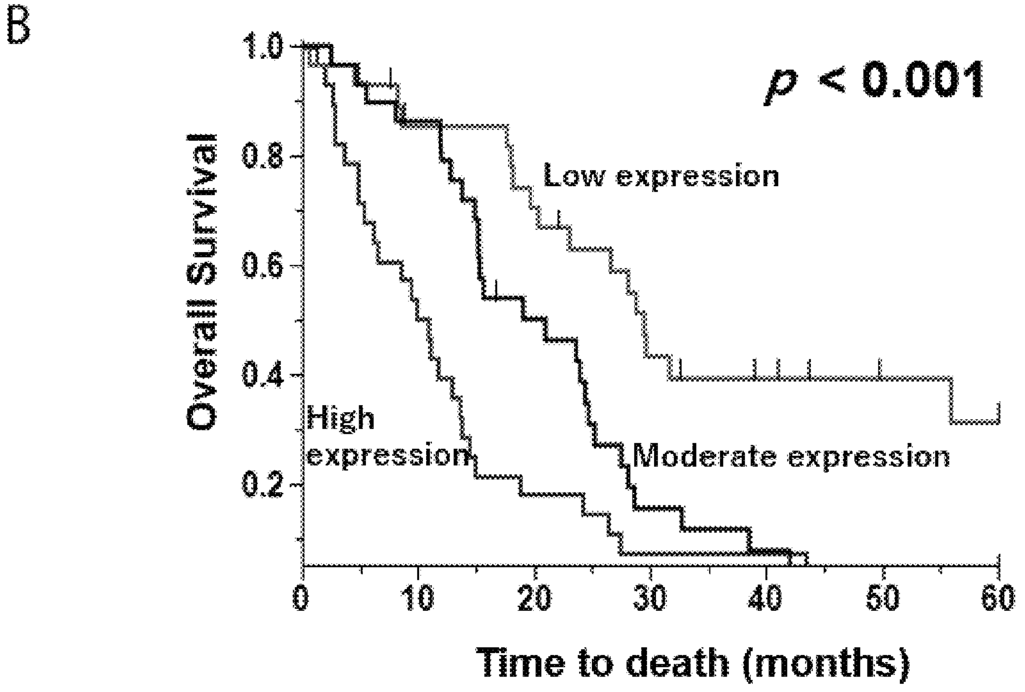
FIG. 2B is diagram illustrating a Kaplan-Meier curve for the overall survival time for a high expression group, a moderate expression group, and a low expression group of oxytocin receptors.

FIG. 2A illustrates a graph indicating the expression level of oxytocin receptors in malignant mesothelioma tissues for the 87 cases of patients having malignant mesotheliomas. It was demonstrated that about 40 percents of the 87 cases of patients having malignant mesotheliomas exhibited higher expression by above 1000 times than the cases of low expression. Further, FIG. 2B illustrates a Kaplan-Meier curve for the overall survival time for a high expression group, a moderate expression group, and a low expression group of oxytocin receptors. As can be seen from FIG. 2B, it was demonstrated that the cases with higher expression of oxytocin receptors tends to have a poorer prognosis. It was therefore demonstrated that a malignant mesothelioma having a poor prognosis has a high expression level of oxytocin receptors.

In Vitro Proliferation Suppression of Malignant Mesothelioma Cell with Cligosiban

Example 3

Next, it was examined whether or not Cligosiban, which is an oxytocin receptor inhibitor, suppresses proliferation of malignant mesothelioma cells in vitro.

The procedure is illustrated below.

(1) Cells of malignant mesothelioma cell line NCI-H2052 were seeded on a dish and cultured for one day.

(2) Cligosiban was administered to the dish at a concentration of 0, 5, 10, 15, 20, or 25 μM.

(3) After culture for five days, evaluation with WST-1 assay was performed. The WST-1 assay is an assay method to administer cell proliferation test agent WST-1 (product number: 11644807001, purchased from Roche) and evaluate cell proliferation by a colorimetric method.

Example 4

The same procedure as that in Example 3 was applied except that the malignant mesothelioma cell line was replaced with NCI-2373 (purchased from ATCC) and Cligosiban was administered to the dish at a concentration of 0, 20, 30, 40, 50, or 60 μM.

Figure 3:
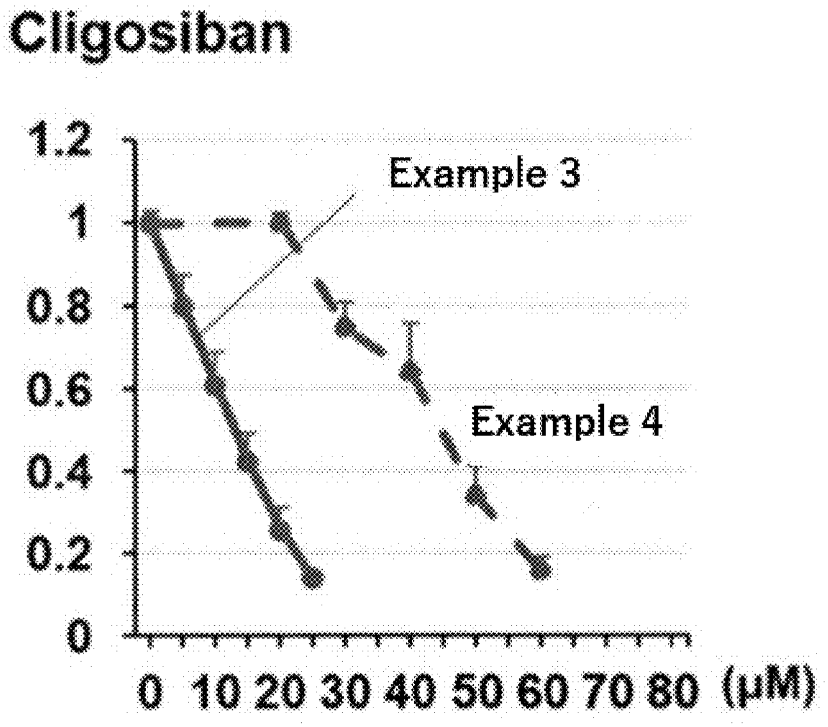
FIG. 3 is a diagram illustrating results of in vitro WST-1 assay of malignant mesothelioma cells to which Cligosiban was administered.

FIG. 3 illustrates the results of WST-1 assay of Example 3 and Example 4. As can be seen from FIG. 3, it was demonstrated that a higher Cligosiban concentration more suppresses proliferation of malignant mesothelioma cells in both Example 3 and Example 4. It was therefore demonstrated that Cligosiban suppresses proliferation of malignant mesothelioma cells both in vivo and in vitro.

Proliferation Suppression of Malignant Mesothelioma Cell with Oxytocin Receptor Inhibitor other than Cligosiban Because it was confirmed that Cligosiban for which effect was confirmed with mice was also effective on two types of malignant mesothelioma cells in vitro, an in vitro experiment system was used to examine whether or not the oxytocin receptor inhibitor other than Cligosiban suppresses proliferation of malignant mesothelioma cells.

Example 5

The same procedure as that in Example 3 was applied except that the oxytocin receptor inhibitor was replaced with OT-R antagonist 1 (purchased from MedChemExpress), which was administered to the dish at a concentration of 0, 20, 40, 60, or 80 μM.

Example 6

The same procedure as that in Example 4 was applied except that the oxytocin receptor inhibitor was replaced with OT-R antagonist 1, which was administered to the dish at a concentration of 0, 20, 40, 60, or 80 μM.

Example 7

The same procedure as that in Example 5 was applied except that the oxytocin receptor inhibitor was replaced with L368,899 hydrochloride (purchased from MedChemExpress).

Example 8

The same procedure as that in Example 6 was applied except that the oxytocin receptor inhibitor was replaced with L368,899 hydrochloride.

Example 9

The same procedure as that in Example 5 was applied except that the oxytocin receptor inhibitor was replaced with Atosiban (purchased from MedChemExpress).

Example 10

The same procedure as that in Example 6 was applied except that the oxytocin receptor inhibitor was replaced with Atosiban.

Figure 4:
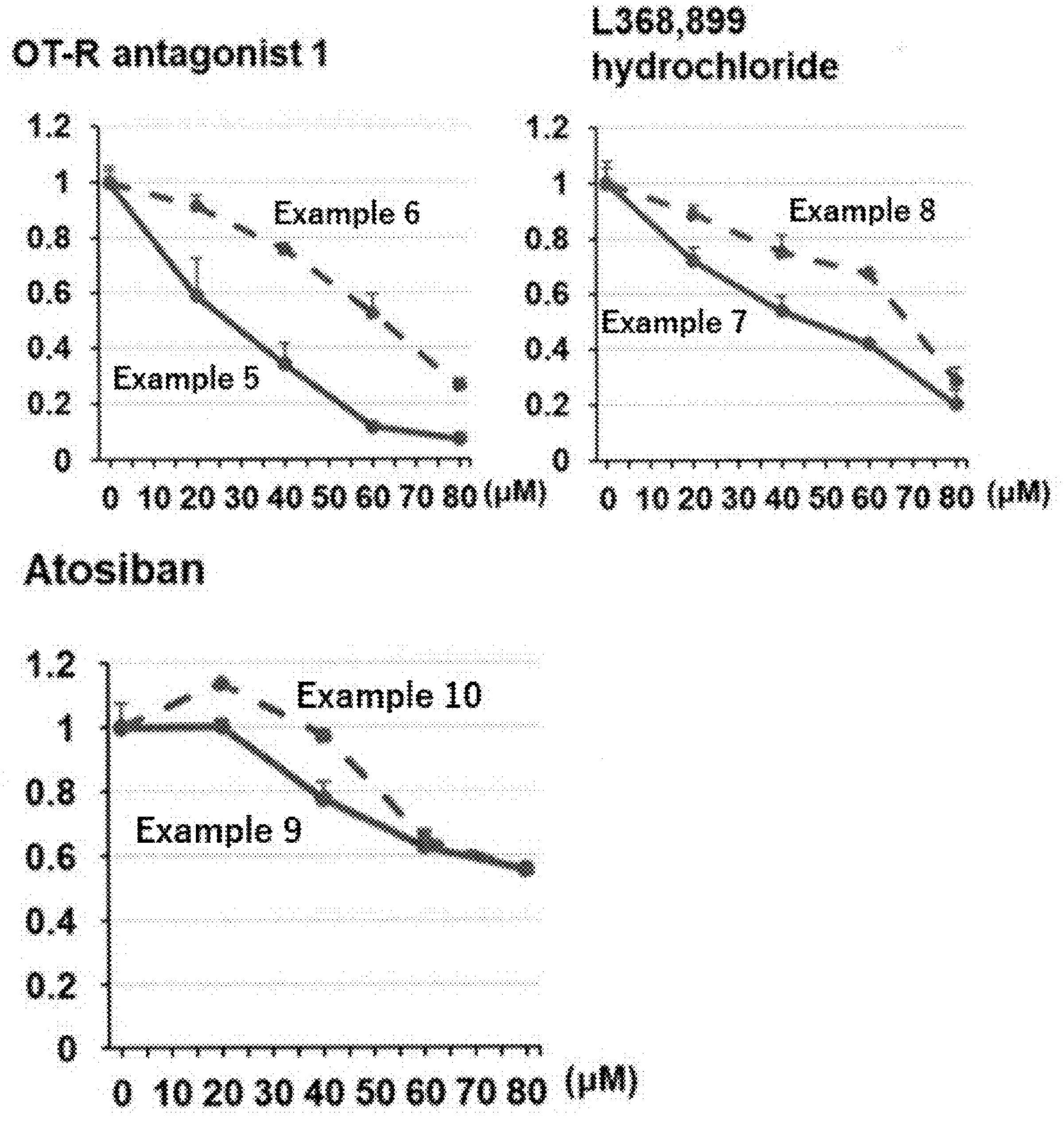
FIG. 4 is a diagram illustrating results of WST-1 assay of malignant mesothelioma cells to which an oxytocin receptor inhibitor was administered.

FIG. 4 illustrates the results of the WST-1 assay of Example 5 to Example 10. As can be seen from FIG. 4, it was demonstrated that a higher concentration of the oxytocin receptor inhibitor more suppresses proliferation of malignant mesothelioma cells in all Example 5 to Example 10. It was therefore demonstrated that the oxytocin receptor inhibitor can be used as a therapeutic agent for malignant mesotheliomas.

Proliferation Suppression of Malignant Mesothelioma Cell by Knockdown of Oxytocin Receptor (1)

It was examined whether or not the siRNA, which is a compound that targets an oxytocin receptor, suppresses proliferation of malignant mesothelioma cells.

Example 11

Proliferation of malignant mesothelioma cells in which oxytocin receptors were knocked down by the siRNA was evaluated by WST-1 assay.

The procedure is illustrated below.

(1) Cells of malignant mesothelioma cell line NCI-H2373 were seeded on a dish and cultured for one day.
(2) Oxytocin receptors were knocked down by using siRNA 1 (product number s9947, purchased from Thermo Fisher Scientific).
(3) After culture for four days, evaluation with WST-1 assay was performed.

Example 12

The same procedure as that in Example 11 was applied except that siRNA 1 was replaced with siRNA 2 (product number s9948, purchased from Thermo Fisher Scientific).

Example 13

The same procedure as that in Example 11 was applied except that the malignant mesothelioma cell line was replaced with NCI-H2052.

Example 14

The same procedure as that in Example 12 was applied except that the malignant mesothelioma cell line was replaced with NCI-H2052.

Comparative Example 2

The same procedure as that in Example 11 was applied except that (1) the malignant mesothelioma cell line was replaced with immortalized cell line MeT-5A (purchased from ATCC) of normal mesothelium and (2) oxytocin receptors were not knocked down.

Comparative Example 3

The same procedure as that in Comparative example 2 was applied except that oxytocin receptors were knocked down by using siRNA 1.

Comparative Example 4

The same procedure as that in Comparative example 2 was applied except that oxytocin receptors were knocked down by using siRNA 2.

Comparative Example 5

The same procedure as that in Example 11 was applied except that oxytocin receptors were not knocked down.

Comparative Example 6

The same procedure as that in Example 13 was applied except that oxytocin receptors were not knocked down.

Figure 5:
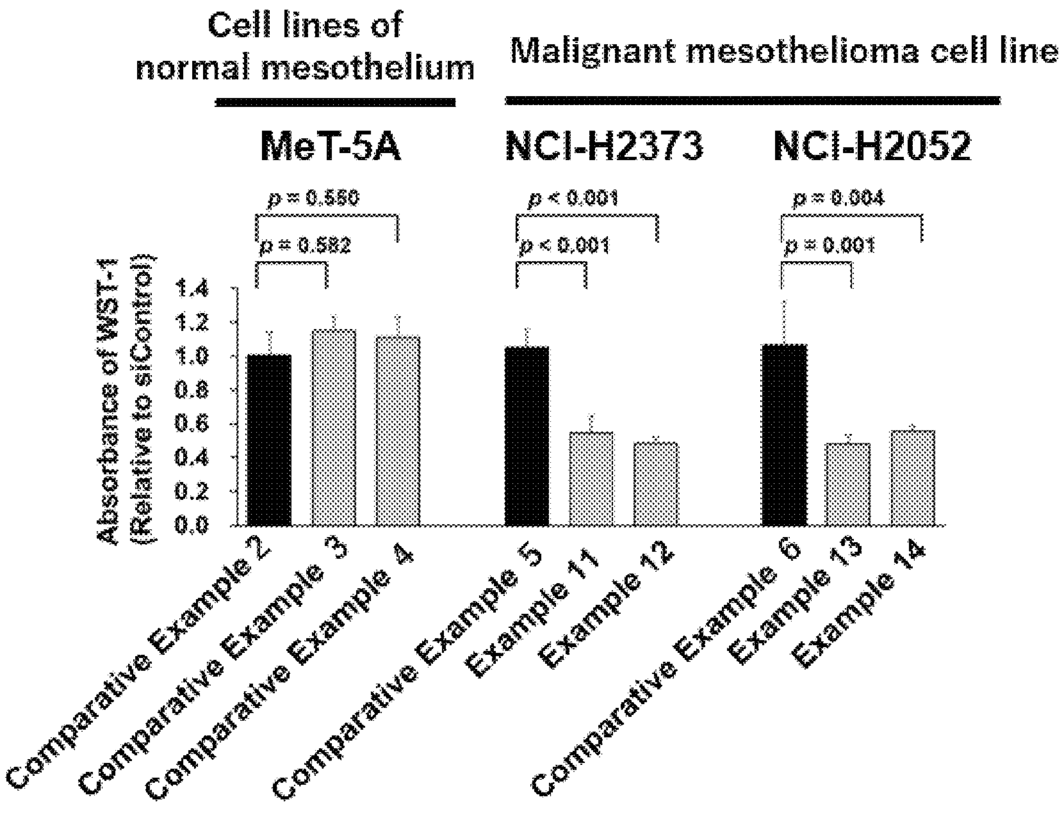
FIG. 5 is a diagram illustrating results of WST-1 assay of malignant mesothelioma cells in which oxytocin receptors were knocked down.

FIG. 5 illustrates the results of the WST-1 assay of Example 11 to Example 14 and Comparative example 2 to Comparative example 6. As can be seen from FIG. 5, it was demonstrated that Example 11 to Example 14 in which oxytocin receptors of malignant mesothelioma cells were knocked down more suppress proliferation of malignant mesothelioma cells than Comparative example 5 and Comparative example 6 in which oxytocin receptors of malignant mesothelioma cells were not knocked down. Further, as can be seen from FIG. 5, for the cell lines of normal mesothelium, Comparative example 3 and Comparative example 4 in which oxytocin receptors were knocked down do not exhibit a significant difference in suppression of the proliferation compared to Comparative example 2 in which oxytocin receptors were not knocked down. Therefore, the siRNA that targets oxytocin receptors was confirmed to be effective for proliferation suppression of malignant mesothelioma cells in which oxytocin receptors were expressed. It was therefore demonstrated that the siRNA that targets oxytocin receptors can be used as a therapeutic agent for malignant mesotheliomas.

Proliferation Suppression of Malignant Mesothelioma Cell by Knockdown of Oxytocin Receptor (2)

Example 15

Proliferation of malignant mesothelioma cells in which oxytocin receptors were knocked down by the siRNA was evaluated by colony formation assay.

The procedure is illustrated below.

(1) Cells of malignant mesothelioma cell line NCI-H2373 were seeded on a dish and cultured for one day.
(2) Oxytocin receptors were knocked down by using siRNA 1.
(3) After 48 hours, cells of NCI-H2373 with oxytocin receptors knocked down were seeded on a new dish.
(4) After culture for two weeks, evaluation with colony formation assay that counts the number of formed colonies was performed.

Example 16

The same procedure as that in Example 15 was applied except that siRNA 1 was replaced with siRNA 2.

Example 17

The same procedure as that in Example 15 was applied except that was the malignant mesothelioma cell line was replaced with NCI-H2052.

Example 18

The same procedure as that in Example 16 was except that is the malignant mesothelioma cell line was replaced with NCI-H2052.

Comparative Example 7

The same procedure as that in Example 15 was applied except that oxytocin receptors were not knocked down.

Comparative Example 8

The same procedure as that in Example 17 was applied except that oxytocin receptors were not knocked down.

Figure 6A:
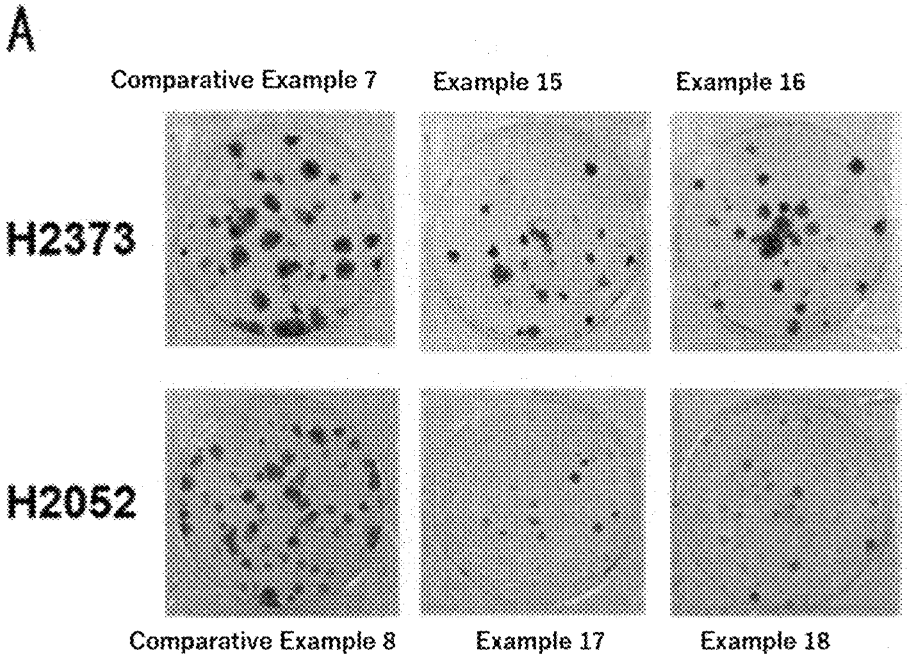
FIG. 6 is a diagram illustrating results of colony formation assay of malignant mesothelioma cells in which oxytocin receptors were knocked down.
Figure 6B:
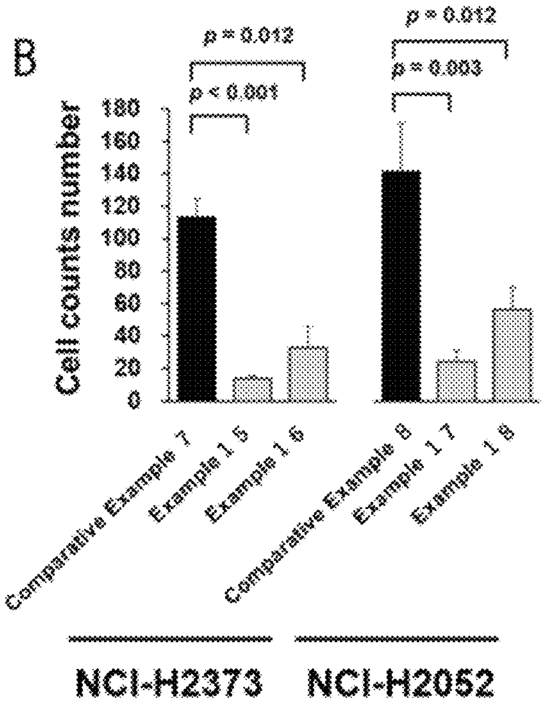

FIG. 6A and FIG. 6B illustrate the results of the colony formation assay of Example 15 to Example 18 and Comparative example 7 and Comparative example 8. As can be seen from FIG. 6A and FIG. 6B, it was demonstrated that Example 15 to Example 18 in which oxytocin receptors of malignant mesothelioma cells were knocked down more inhibit colony formation than Comparative example 7 and Comparative example 8 in which oxytocin receptors of malignant mesothelioma cells were not knocked down. It was therefore demonstrated that Example 15 to Example 18 suppress proliferation of malignant mesothelioma cells as with Example 11 to Example 14.

Proliferation Suppression of Malignant Mesothelioma Cell by Knockdown of Oxytocin Receptor Using Xenograft Model Example 19

It was examined whether or not the shRNA that constantly knocks down oxytocin receptors suppresses proliferation of malignant mesothelioma cells in vivo.

The procedure is illustrated below.

(1) Three types of plasmids of pMD2.G (Plasmid #12259, purchased from Addgene), psPAX2 (Plasmid #12260, purchased from Addgene), and pLKO.1 puro with shRNA construct (Plasmid #10878, purchased from Addgene) in which a sequence that knocks down oxytocin receptors were incorporated were transfected into 293FT cell line (purchased from Thermo Fisher) to produce a lentivirus.
(2) Cells of malignant mesothelioma cell line NCI-H2373 were seeded on a dish and cultured for one day.
(3) The lentivirus produced in (1) described above was used to introduce the shRNA into NCI-H2373 and constantly knock down oxytocin receptors.
(4) NCI-H2373 in which oxytocin receptors were knocked down was cultured.
(5) $1.5\times10^6$ cells of NCI-H2373 in which the cultured oxytocin receptors were knocked down were administered to the subcutaneous left buttock of nude mice (BALB/c nude (nu/nu) female, 6 weeks old: purchased from Charles River Japan).
(6) After one month from the subcutaneous administration, the nude mice were dissected, and the subcutaneous tumor weights were measured.

Example 20

The same procedure as that in Example 19 was applied except that the malignant mesothelioma cell line was replaced with NCI-H2052.

Comparative Example 9

The same procedure as that in Example 19 was applied except that oxytocin receptors were not knocked down by using the lentivirus, which was produced by replacing, with Scramble shRNA (Plasmid #1864, purchased from addgene), the pLKO.1 puro with shRNA construct implanted with the sequence that knocks down oxytocin receptors.

Comparative Example 10

The same procedure as that in Example 20 was applied except that oxytocin receptors were not knocked down by using the lentivirus, which was produced by replacing, with Scramble shRNA, the pLKO.1 puro with shRNA construct implanted with the sequence that knocks down oxytocin receptors.

Figure 7:
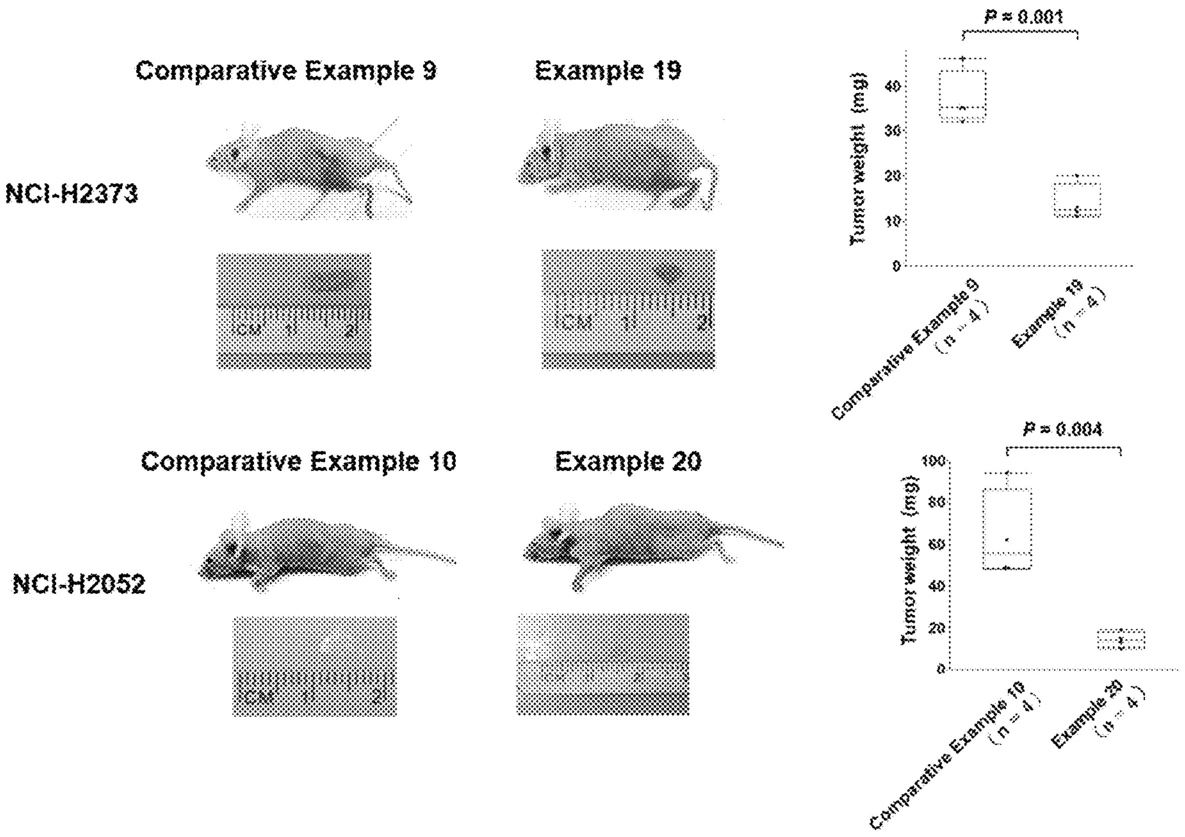
FIG. 7 is a diagram illustrating results of proliferation suppression of malignant mesothelioma cells in which oxytocin receptors were knocked down using the Xenograft model.

FIG. 7 illustrates the results. As can be seen from FIG. 7, it was demonstrated that the subcutaneous tumor weights of both Example 19 and Example 20 in which oxytocin receptors were knocked down are smaller than that of Comparative example 9 and Comparative example 10 in which oxytocin receptors were not knocked down. It was therefore demonstrated that the shRNA that targets oxytocin receptors can be used as a therapeutic agent for malignant mesotheliomas.

Proliferation Suppression of Malignant Mesothelioma Cell by Combined Use of Compound Targeting Oxytocin Receptor and Anticancer Agent Example 21

Proliferation suppression of malignant mesothelioma cells by combined use of Cligosiban and cisplatin was evaluated by WST-1 assay.

The procedure is illustrated below.

(1) Cells of malignant mesothelioma cell line NCI-H2373 were seeded on a dish and cultured for one day.

(2) Cligosiban 45 μM and cisplatin (product number 033-20091, purchased from FUJIFILM Wako Pure Chemical Corporation) 6 μM were administered to the dish.

(3) After culture for five days, evaluation with WST-1 assay was performed.

Example 22

The same procedure as that in Example 21 was applied except that only Cligosiban 45 μM was administered.

Example 23

The same procedure as that in Example 21 was applied except that the malignant mesothelioma cell line was replaced with NCI-H2052 and that Cligosiban 15 μM and cisplatin 0.8 μM were administered to the dish.

Example 24

The same procedure as that in Example 22 was applied except that the malignant mesothelioma cell line was replaced with NCI-H2052 and that Cligosiban 15 μM was administered.

Comparative Example 11

The same procedure as that in Example 21 was applied except that neither Cligosiban 45 μM nor cisplatin 6 μM was administered.

Comparative Example 12

The same procedure as that in Example 21 was applied except that only cisplatin 6 μM was administered.

Comparative Example 13

The same procedure as that in Example 23 was applied except that neither Cligosiban 15 μM nor cisplatin 0.8 μM was administered.

Comparative Example 14

The same procedure as that in Example 23 was applied except that only cisplatin 0.8 μM was administered.

Figure 8:
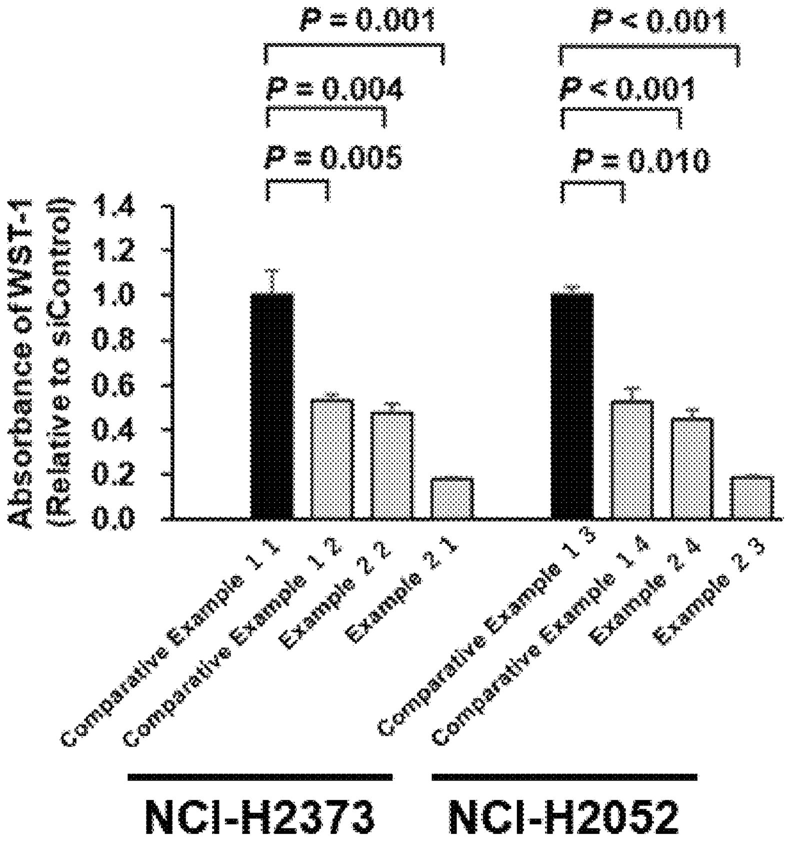
FIG. 8 is a diagram illustrating results of WST-1 assay of malignant mesothelioma cells to which a compound that targets oxytocin receptors and an anticancer agent were administered.

FIG. 8 illustrates the results of WST-1 assay of Example 21 to Example 24 and Comparative example 11 to Comparative example 14. As can be seen from FIG. 8, it was demonstrated that Example 21 to Example 24 and Comparative example 12 and Comparative example 14 in which both or either one of Cligosiban and cisplatin was administered to malignant mesothelioma cells more suppresses proliferation of malignant mesothelioma cells than Comparative example 11 and Comparative example 13 in which neither Cligosiban nor cisplatin was administered. Further, it was demonstrated that Example 21 and Example 23 in which both of Cligosiban and cisplatin were administered more suppress proliferation of malignant mesothelioma cells than Example 22, Example 24, Comparative example 12, and Comparative example 14 in which either one of Cligosiban and cisplatin was administered.

From Example 1 to Example 24 described above, it was found that the compound that targets oxytocin receptors can be used as a therapeutic agent for malignant mesotheliomas. Further, the compound that targets oxytocin receptors was effective against malignant mesotheliomas that express oxytocin receptors. It was therefore demonstrated that companion diagnosis for the therapeutic agent may be made possible by measuring the expression level of oxytocin receptors in a malignant mesothelioma tissue of a patient having a malignant mesothelioma.

Proliferation Suppression of Malignant Mesothelioma Cell by Existing Standard Therapeutic Drug for Malignant Mesothelioma, Cligosiban, and Combined Use of Existing Standard Therapeutic Drug and Cligosiban Example 25

Examined was proliferation suppression of malignant mesothelioma cells when Cligosiban was further used in combination with a concomitant medication of cisplatin and pemetrexed that are existing standard therapeutic drugs for malignant mesotheliomas.

The procedure is illustrated below.

(1) $5.0\times10^6$ cells of malignant mesothelioma cell line NCI-H2052 (purchased from ATCC) were administered to the subcutaneous left buttock of nude mice (BALB/c nude (nu/nu) female, 6 to 8 weeks old: purchased from Charles River Japan).

(2) After 7 days from the subcutaneous administration, oral administration of Cligosiban (purchased from MedChemExpress) was started, and the oral administration was applied at each dose of 60 mg/kg every other day for a total of 10 doses.

(3) After 7 days from the subcutaneous administration, cisplatin (product number 033-20091, purchased from FUJIFILM Wako Pure Chemical Corporation) 2 mg/kg and pemetrexed disodium heptahydrate (product number 161-26263, purchased from FUJIFILM Wako Pure Chemical Corporation) 25 mg/kg were once injected into a tail vein.

(4) After two days from the tenth oral administration of Cligosiban, the nude mice were dissected, and the subcutaneous tumor weights were measured.

Example 26

The same procedure as that in Example 25 was applied except that neither cisplatin nor pemetrexed was administered.

Comparative Example 15

The same procedure as that in Example 25 was applied except that neither Cligosiban nor cisplatin and pemetrexed was administered.

Comparative Example 16

The same procedure as that in Example 25 was applied except that Cligosiban was not administered.

Figure 9:
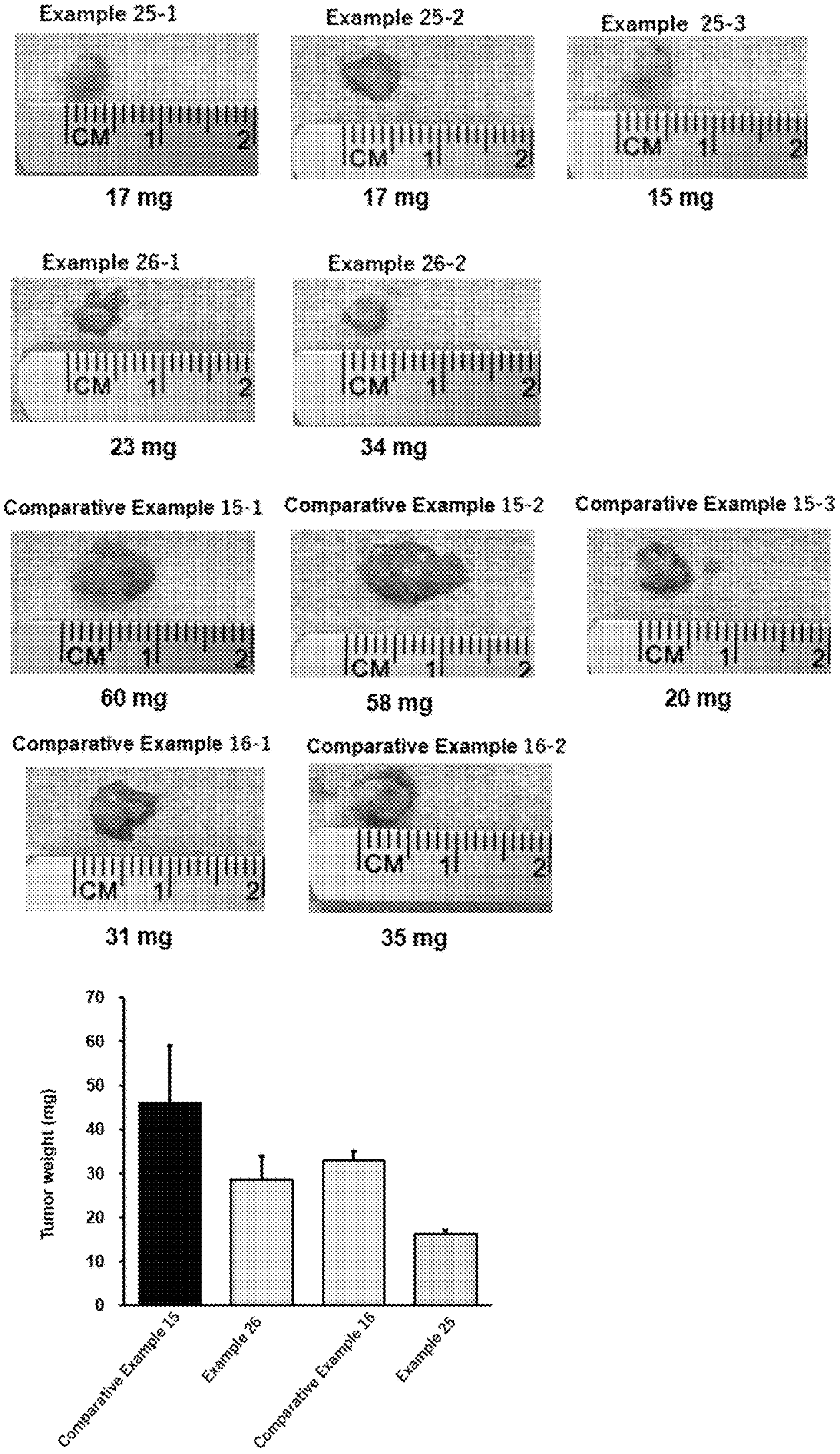
FIG. 9 is a diagram illustrating results of proliferation suppression of malignant mesothelioma cells with use of an existing standard therapeutic drug for a malignant mesothelioma, use of Cligosiban, and combined use of the existing standard therapeutic drug and Cligosiban by using the Xenograft model.

FIG. 9 illustrates the results. Note that three nude mice were used in Example 25. Thus, respective tumors removed from the nude mice are labeled with Example 25-1 to Example 25-3. Further, two nude mice were used in Example 26, three nude mice were used in Comparative example 15, and two nude mice were used in Comparative example 16, and numbers are applied thereto in the same manner as Example 25.

As illustrated in FIG. 9, the subcutaneous tumor weight of Example 26 with administration of Cligosiban was smaller than the subcutaneous tumor weight of Comparative example 16 with administration of cisplatin and pemetrexed that are existing standard therapeutic drugs for malignant mesotheliomas. Surprisingly, it was demonstrated that Cligosiban, even when used alone, is more effective than the existing standard therapeutic drugs.

Furthermore, in Example 25 in which Cligosiban together with cisplatin and pemetrexed are used in combination, it was demonstrated that the subcutaneous tumor weight is significantly smaller than that of Example 26 and Comparative example 16. It was therefore demonstrated that the combined used of Cligosiban with the existing therapeutic drug for malignant mesotheliomas achieves a notable therapeutic effect that is unpredictable from the conventional art.

INDUSTRIAL APPLICABILITY

The disclosure is useful in the field of treatment of malignant mesotheliomas for which no effective therapeutic agent or treatment method has been established so far.

The invention claimed is:

1. A method of treatment for a malignant mesothelioma, the method of treatment comprising administering to a patient a therapeutic agent comprising, as an active ingredient, a compound that targets an oxytocin receptor, wherein the compound is an oxytocin receptor inhibitor, and wherein the oxytocin receptor inhibitor is Cligosiban.

2. The method of treatment according to claim 1, wherein the therapeutic agent further comprises an anticancer agent.

3. The method of treatment according to claim 2, wherein the anticancer agent is cisplatin.

4. The method of treatment according to claim 2, wherein the anticancer agent comprises cisplatin and pemetrexed.

5. A method of treatment for a malignant mesothelioma, the method of treatment comprising administering to a patient a therapeutic agent comprising, as an active ingredient, a compound that targets an oxytocin receptor, wherein the compound is an oxytocin receptor inhibitor, and wherein the oxytocin receptor inhibitor is OT-R antagonist 1.

6. The method of treatment according to claim 5, wherein the therapeutic agent further comprises an anticancer agent.

7. The method of treatment according to claim 6, wherein the anticancer agent is cisplatin.

8. The method of treatment according to claim 6, wherein the anticancer agent comprises cisplatin and pemetrexed.

* * * * *